United States Patent [19]

Fazzalari

[11] 3,992,146

[45] Nov. 16, 1976

[54] PROCESS OF USING BIOCIDAL SOLUTIONS CONTAINING COPPER SULFATE

[76] Inventor: Frank A. Fazzalari, Box 1746, Poughkeepsie, N.Y. 12601

[22] Filed: July 30, 1974

[21] Appl. No.: 493,180

Related U.S. Application Data

[63] Continuation-in-part of Ser. No. 180,065, Sept. 13, 1971, abandoned.

[52] U.S. Cl. .................................. 21/58; 252/106; 424/141; 424/143

[51] Int. Cl.$^2$ .................... A61K 33/34; A61L 9/00; C11D 3/48

[58] Field of Search ...................... 21/58; 134/2, 40; 71/67, 4; 252/106, 107; 424/141, 143

[56] References Cited

UNITED STATES PATENTS

| | | | |
|---|---|---|---|
| 383,853 | 6/1888 | Belcher | 252/133 |
| 2,121,485 | 6/1938 | McAllister et al. | 252/106 |
| 2,157,861 | 5/1939 | Nikitin et al. | 21/58 X |
| 2,160,834 | 6/1939 | Corbett | 252/107 |
| 2,241,790 | 5/1941 | Rembert | 134/40 X |
| 2,264,212 | 11/1941 | Large | 424/143 |
| 3,179,599 | 4/1965 | Eaton et al. | 252/153 |
| 3,197,313 | 7/1965 | Greiner | 21/58 UX |
| 3,505,112 | 4/1970 | Kettler | 21/58 X |
| 3,705,103 | 12/1972 | Cohen | 134/2 X |
| 3,784,357 | 1/1974 | Muraoka | 21/58 X |

OTHER PUBLICATIONS

Chem. Abstracts; "17–Pharmaceuticals, Cosmetics, Perfumes"; 1951; 6801h.

McCutcheon; "Detergents & Emulsifiers"; 1969.

*Primary Examiner*—Morris O. Wolk

*Assistant Examiner*—Bradley Garris

*Attorney, Agent, or Firm*—Donald F. Clements

[57] ABSTRACT

Growth of fungus such as mold and mildew fungi is inhibited by applying to the surface to be protected an aqueous solution of a copper compound, such as copper sulfate, and a surfactant. The aqueous solution of copper compound and surfactant is especially effective for inhibiting the growth of microorganisms on hard porous surfaces such as grout seams associated with bathroom components such as bath tubs and ceramic tile shower stalls which are exposed to high humidity conditions for extended periods.

In one embodiment, growth of microorganisms is inhibited by applying the aqueous solution of copper compound and surfactant to hard porous surfaces in need of treatment. In another embodiment of the invention, an aqueous solution of copper compound and surfactant is used as the liquid source for forming the uncured mortar used to install or replace tiles.

6 Claims, No Drawings

PROCESS OF USING BIOCIDAL SOLUTIONS CONTAINING COPPER SULFATE

This application is a continuation-in-part of my copending application Ser. No. 180,065 filed Sept. 13, 1971 and now abandoned.

This invention relates to germicides containing copper derivatives and to a process for inhibiting the growth of microorganisms therewith.

A serious problem in many households and public bathing facilities is the difficulty encountered in controlling growth of microorganisms. This growth is not only detrimental to health but also presents an unsightly appearance when formed on grout seams associated with bathtubs, ceramic tiles and the like. Because of the porous nature of the grout, water may collect in the pores and provide fertile sites for growth of microorganisms. Frequent brushing and scraping of the surfaces becomes necessary because of the deep penetration of mold, mildew and the like into the pores. Soft surfaces such as grout seams rapidly deteriorate under these circumstances and frequent replacement is necessary to keep the tiles in place and to avoid penetration of water into the walls and sub-flooring.

Copper compounds have been used for many years to inhibit the growth of fungus. For example, U.S. Pat. No. 43,233, issued June 21, 1864, disclosed inhibiting mildew in sails by immersing the sails in an aqueous solution of copper sulfate. This technique is not possible with grout seams, bathroom walls and the like. U.S. Pat. No. 2,264,212, issued Nov. 25, 1941, discloses a foilage fungicide comprised of a dispersion containing a basic copper chloride on bentonite. This technique is not readily adaptable to the treatment of materials such as grout seams since a solid dispersion of bentonite on the grout seams and bathtub would be as unattractive as the mold itself.

V. Engler et al. *Pharm. Acta. Helv.* 26, pp. 59–67 (1951) disclose that a mixture of copper sulfate and a nitrogen-free surfactant such as sodium-dioctyl-sulfosuccinate have a fungicidal effect in acid media, at a pH of about 4.6. However, some nitrogen-free surfactants have been found to be reactive with copper sulfate and form precipitates in aqueous solutions, especially during storage.

McAllister et al. U.S. Pat. No. 2,121,485, issued June 21, 1938, disclose complexes of copper with a fatty acid amide of methyl taurine. The aqueous solution contains excessive amounts of the complex since it is distinctively colored aqua, thereby limiting its use as a fungicide on light surfaces.

There is a need at the present time for an aqueous copper-based fungicide solution which is capable of penetrating porous surfaces without imparting the natural color of the copper to the surface being treated.

It is a primary object of this invention to prepare a new germicidal composition.

A further object of the invention is to provide a novel aqueous fungicidal composition suitable for preparing uncured grout material used in the repair or installation of bathroom tiles and the like.

Another object of this invention is to provide a process for inhibiting growth of fungi on porous surfaces.

Still another object of the invention is to provide a process for treating grout seams of bathing facilities to inhibit growth of germs.

These and other objects of the invention will be apparent from the following detailed description.

It has now been discovered that the aforesaid objects are accomplished by applying to a hard porous surface to be protected against microorganisms, an aqueous solution of a copper compound and a surfactant which facilitates penetration of the porous surface by the solution. Formation of microorganisms such as mold and mildew fungi is greatly inhibited or completely retarded by use of the novel composition and process of this invention.

In another embodiment of the invention, an aqueous solution of copper compound which preferably contains a surfactant is used as the aqueous medium to prepare a fluid grout, plaster, caulk or cement mixture, which will cure to form a hard porous compound impregnated with copper compound to prevent the formation of mold and mildew fungi.

More in detail, the germicidal solution is prepared by dissolving in water a water soluble copper compound. Copper sulfate is the preferred copper compound because of its superior effectiveness and its lower cost. For this reason, the invention will be described using copper sulfate as the water soluble copper compound. However, other suitable copper compounds include cupric acetate, cupric ammonium chloride, cupric perchloride, including the anhydrous and dihydrate and thiourea forms, cupric dichromate, cupric fluoride, cupric formate, cupric iodate monohydrate, cupric lactate, cupric nitrate, including the trihydrate forms, cupric selenate, cupric silicofluoride, and mixtures thereof.

Sufficient copper sulfate is added to form an aqueous solution having a concentration of between about 0.1 ppm and the concentration of a saturated solution at ambient temperatures, and preferably between about 100 ppm and about 100,000 ppm of copper sulfate. However, if the aqua color is objectionable, which sometimes appears on the treated surface when high concentrations are used, the concentration should be between about 100 ppm and about 10,000 ppm of copper sulfate. If other copper compounds are used instead of copper sulfate, similar proportions can be used.

Another component of the germicidal solution is a small proportion of a surfactant to facilitate penetration of the solution into porous surfaces to be protected such as, grout seams between ceramic tiles, concrete, plaster or other porous surfaces found in bathrooms and other high humidity areas. As used throughout the description and claims, the term "surfactant" includes wetting agents, detergents, penetrants and any other agents capable of facilitating the penetration of the pores of the surface to be protected by the aqueous copper sulfate solution. In general, any water soluble anionic surfactant is suitable. For example, suitable surfactants of this type are disclosed in *Surface Chemistry — Theory and Industrial Applications* by Lloyd L. Osipow, Reinhold Publishing Corporation, (1962) and in *Systematic Analysis of Surface-Active Agents*, by Milton J. Rosen and Henry A. Goldsmith, Interscience Publishers, Inc. (1960).

Suitable surfactants include the following:

A. Soaps
  1. Alkali metal soaps
    a. Sodium oleate
    b. Sodium laurate c. Sodium myristate
d. Potassium oleate
e. Potassium laurate
f. Potassium myristate
2. Ammonia Soaps
a. Mono-ethanolamine
b. Di-ethanolamine
c. Tri-ethanolamine
d. Morpholine
e. Isopropanolamines
f. Water-soluble alkyl amines
3. Inorganics
a. Tetrasodium pyrophosphate
b. Sodium hexametaphosphate
c. Sodium tripolyphosphate B. Sulfonates
1. Alkylbenzene sulfonates
a. Sodium dodecylbenzene sulfonate
b. Sodium propylenetetramer benzene sulfonate
c. Sodium tridecylbenzene sulfonate
d. Sodium pentadecylbenzene sulfonate
2. Dialkyl esters of sodium sulfosuccinic acid (alkyl containing about 5 to about 20 carbon atoms)
a. Sodium didodecyl sulfosuccinate
b. Sodium diamyl sulfosuccinate
c. Sodium dihexyl sulfosuccinate
d. Sodium di(2-ethylhexyl) sulfosuccinate
e. 2-butyloctyldiester of sodium sulfosuccinic acid
3. Metal salts of monoamides of sulfodicarboxylic acids
a. $NaOOCCH_2CH(SO_3Na)CONCH_{18}H_{37}$
b. $NaOOCH(SO_3Na)CH_2CON(C_{18}H_{37})CH(COONa)CH_2COONa$ (Aerosol 22)
4. Fatty acid chloride plus sodium isethionate
a. Sodium β-oleylethanesulfonate
b. $RCOOC_2H_4SO_3Na$ (oleic acid derivative)
c. $RCOOC_2H_4SO_3Na$ (coconut f.a. derivative)
5. Fatty acid amides of sulfonated polyhydric aliphatic alcohols, such as methyl taurine and cyclohexyl taurine
a. $RCON(R')C_2H_4SO_3Na$ (R from oleic acid; $R'=CH_3$)
b. $RCON(R')C_2H_4SO_3Na$ (R from tall oil; $R'=CH_3$)
c. $RCON(R')C_2H_4SO_3Na$ (R from palmitic acid; $R'=CH_3$)
d. $RCON(R')C_2H_4SO_3Na$ (R from palmitic acid; R'= cyclohexyl)
6. Pentaerythritol monoesters
a. Pentaerythritol monostearate
b. Pentaerythritol monolaurate
7. Alkylnaphthalene sulfonic acids
a. Isobutylnaphthalene sulfonate
8. Alkyl aromatic sulfonates
a. Alkyl toluene sulfonate
b. Alkyl xylene sulfonate
9. Petroleum sulfonates
a. Alkylaryl alkyl and aryl sodium sulfonates C. Sulfates
1. Sulfated branched-chain alcohols
a. 2-butyl-2-ethyl-ethyl sodium sulfonate
b. 1-dimethyl-ethyl-4-butyl-4-ethyl-butyl sodium sulfonate
c. 1-diethyl-propyl-4-butyl-4-ethyl-butyl sodium sulfonate
2. Monosulfate of a monoglyceride
a. Sodium glyceryl monolaurate sulfate
3. Sulfated alkylphenoxyethanol
a. Sodium alkylphenoxyethylsulfate (alkyl groups consist of 8 or 9 carbon atoms)
4. Sulfated alkylphenoxyethoxyethanol
a. Sodium alkylphenoxyethoxyethysulfate (alkyl groups consist of 8 or 9 carbon atoms)
5. Alkyl sulfates
a. Sodium lauryl sulfate
b. Ammonium lauryl sulfate
6. Sulfated aliphatic esters (sulfonated oils)
a. Sodium glyceryl-triricinoleyl sulfate (turkey red oil)

D. Unbuilt, high-sudsing, light-duty liquid detergent compositions
1. Liquid detergents of the type described in U.S. Pat. No. 3,179,598, which issue Apr. 20, 1965. These liquid detergent compositions consist essentially of:
a. from about 20 to about 40% by weight of the composition of a sulfate detergent surfactant having the following formula $$R-(C_2H_4O)_x-SO_4-Me$$

wherein R is a straight chain alkyl group having from about 10 to about 14 carbon atoms with at least 50% of said alkyl groups having 12 carbon atoms, $x$ is a number from zero to about four, and Me is selected from the group consisting of monoethanolamine, diethanolamine, triethanolamine, ammonium, sodium and potassium cations,
b. a trialkyl amine oxide having one straight chain alkyl group having from about 10 to about 14 carbon atoms with at least 50% of said alkyl groups having 12 carbon atoms and two short chain alkyl groups having from one to about two carbon atoms in an amount such that the weight ratio of sulfate detergent surfactant to amine oxide is from 3/1 to 7/1,
c. at least about 50% by weight of the composition of solubilizing agent selected from the group consisting of methyl, ethyl, n-propyl, and isopropyl alcohol,
d. and the balance water. Other minor ingredients including from zero to about 5% by weight of the composition of a viscosity control agent such as either potassium, sodium, or ammonium toluene sulfonate or potassium, sodium or ammonium xylene sulfonate; perfume; opacifiers; and coloring can be added.
2. Liquid detergent compositions of the type described in U.S. Pat. No. 3,179,599, which issued Apr. 20, 1965. These compositions consist essentially of:
a. from about 20 to about 40% by weight of the composition of a sulfate detergent surfactant having the following formula $$R-(C_2H_4O)_x-SO_4-Me$$

wherein R is a straight chain alkyl group having from about 10 to about 14 carbon atoms with at least 50% of said alkyl groups having 12 carbon atoms, $x$ is a number from zero to about four, and Me is selected from the group consisting of monoethanolamine, diethanolamine, triethanolamine, ammonium, sodium, and potassium cations, b. from about 5 to about 20% by weight of the composition of a trialkyl amine oxide having one straight chain alkyl group having from about 10 to about 14 carbon atoms and two short chain alkyl groups having 12 carbon atoms and two short chain alkyl groups having from one to about two carbon atoms in an amount such that the weight ratio of sulfate detergent surfactant to amine oxide is from about 1/1 to about 7/1,
c. from about 2% to about 10% by weight of the composition of an alkyl glyceryl ether sulfonate having a straight chain alkyl group having from about 10 to about 14 carbon atoms with at least 50% of said alkyl groups having 12 carbon atoms, the cation of said sulfonate being selected from the group consisting of monoethanolamine, diethanolamine, triethanolamine, ammonium, sodium, and potassium cations and mixtures thereof, the amount of said sulfonate being at least 20% of the amount of said amine oxide,
d. at least about 5% by weight of the composition of a solubilizing agent selected from the group consisting of methyl, ethyl, n-propyl, and isopropyl alcohols,
e. and the balance water. Other minor ingredients include from zero to about 5% by weight of the composition of a viscosity control agent such as either potassium, sodium or ammonium toluene sulfonate or potassium, sodium or ammonium xylene sulfonate; perfume; opacifiers; and coloring can be added.

3. Liquid detergents containing sulfonated aliphatic glyceryl ethers of the type described in U.S. Pat. No. 3,024,273.

E. Other suitable surfactants include
1. Sodium carboxymethyl cellulose
2. Sodium sulfosuccinate
3. 1-lauryl-3-ethylbenzotriazolium bromide
4. Lauryl monoethanolamine
5. Lauryl monoisopropanolamide
6. Salts of α-sulfostearic acid
7. Salts of α-sulfopalmitic acid Water soluble anionic nitrogen-containing surfactants such as the fatty acid amides of sulfonated polyhydric alcohols of the type illustrated above under B:5-a-d, detergents such as unbuilt, high-sudsing, light-duty liquid detergent compositions of the type described above under D:1-3, ammonium lauryl sulfate and mixtures thereof are preferred surfactants because of their stability in aqueous solutions of copper sulfate and their effectiveness in facilitating the penetration of the porous surface by the aqueous germicidal solution. As indicated in the formulation of U.S. Pat. Nos. 3,179,598 and 3,179,599 described above commercial surfactants are frequently a mixture of two or more components. Other illustrations include a surfactant sold under the brand name of Orvus K by Proctor and Gamble, which has the following composition:

| Component | Per Cent by Weight |
|---|---|
| Ammonium Lauryl Sulfate | 37.5% |
| *Alkynol Amide | 9.0% |
| Ammonium Sulfate | 0.9% |
| Ammonium Chloride | 1.0% |
| Ethanol | 21.2% |

-continued

| Component | Per Cent by Weight |
|---|---|
| Water | 30.4% |

*amide of sodium sulfonate of $C_{10}$, $C_{12}$, $C_{14}$, and $C_{16}$ alcohols.

Another suitable surfactant composition is sold under the trademark, Igepon T-33 by General Aniline and Film Corp., having the following composition:

| Component | Per Cent by Weight |
|---|---|
| sodium-N-methyl-N-oleoyl taurate | 32% |
| sodium chloride | 7-9% |
| sodium sulfate | trace |
| sodium oleate | 3% |
| water | 50% |

When proportions of surfactants are used throughout the description and claims, the proportion not only refers to pure surfactant materials but also to commercial surfactants, which may contain two or more components of the type described above. In addition, two or more surfactants may be included in the aqueous copper sulfate solution and used as the surfactant component of the germicidal solution of this invention.

Any effective proportion of surfactant capable of improving the penetration of the porous surface to be treated by the aqueous copper sulfate solution may be employed. The effective proportion of surfactant will not necessarily be the same for each surfactant or type of surfactant. Generally an effective proportion is that amount which will reduce the surface tension of the aqueous germicidal solution to below about 35 dynes/cm., and preferably below about 30 dynes/cm. For example, when the surfactant is of the sodium sulfocuccinic acid ester type such as $NaOOCCH(SO_3Na)—CH_2CON(C_{18}H_{37})CH(COONa)CH_2COONa$ (Aersol 22), the proportion may range from about 0.05 to about 5% and preferably from about 0.08 to about 2.5% by weight of the aqueous copper sulfate solution.

However, when the surfactant is of the detergent type such as liquid detergents of the type described in U.S. Pat. Nos. 3,179,598 and 3,179,599 or of the fatty acid amide type such as the sodium salt of the fatty acid amide of methyl taurine, or ammonium lauryl sulfate, an effctive proportion is from about 1 to about 6%, and preferably from about 2 to about 5% by weight of the aqueous copper sulfate solution.

Thus it can be seen that the effective proportion of surfactant generally ranges from about 0.05 to about 6% and preferably from about 0.08 to about 5% by weight of the aqueous copper sulfate solution, the desirable proportion of wetting agent type surfactant being in the lower parts of the ranges, and the desirable proportion of the detergent type surfactant being in the upper parts of the ranges.

If desired, other additives such as optical bleaches (bluing) may be added in small but effective proportion to the aqueous copper sulfate solution. Generally between about 40 and about 160 drops and preferably between about 50 and about 100 drops of bluing per gallon of aqueous germicidal solution are employed.

A variety of techniques may be employed in applying the aqueous germicidal solution to the hard porous surface such as grout, plaster, cement, or caulk to be protected. In one embodiment, the aqueous germicidal solution is sprayed or wiped onto the porous surface to be protected and a brush is applied to any fungus or dirt that may already adhere to the porous surface. After allowing the aqueous germicidal solution to remain on the surface for at least about 2 and preferably from about 3 to about 10 minutes, or any other convenient period, the excess solution is wiped off with a damp cloth. The surfactant component of the aqueous germicidal solution facilitates penetration of the solution into the pores. Extended protection against the formation of fungus is thus obtained on the surface and in the pores, not only because of the presence of copper sulfate, but also because of the formation of tribasic copper sulfate which forms on the surface and in the pores. Without being bound by theory, it is believed that the copper sulfate originally present in the aqueous germicidal solution reacts with components of the grout, plaster, or cement such as lime or other alkaline hydroxides to form a water insoluble complex such as tribasic cupric sulfate on the surface and in the interior of the grout, plaster or cement. This complex, as well as unreacted copper sulfate which impregnates the porous substance acts as a germicide and inhibits or retards the formation of mold or fungus on the surface and in the pores.

For convenience purposes, the term, "tribasic cupric sulfate" will be used throughout the description and claims to define the reaction product of copper sulfate in the aqueous germicidal solution with lime or other hydroxides that may be present in the caulk, grout, plaster or cement. Although this reaction product may have a chemical composition other than that corresponding to the empirical formula for tribasic cupric sulfate, it is this reaction product that effectively inhibits the growth of fungus, algae and bacteria in and on the porous substance.

In another embodiment of the ianvention, when fresh grout, caulk, plaster or cement is prepared which requires water to formulate, the water is replaced with an aqueous solution of copper sulfate and preferably a small but effective proportion of a surfactant. For example, the proportion of surfactant in the Mortar Mix range from about 0.001 to about 0.5% by weight of surfactant, but greater or lesser quantities can be used if desired. The copper sulfate concentration in solutions used to prepare grout, plaster, caulk, or cement ranges from about 100 to about 100,000 ppm. At higher concentrations the resulting grout, plaster, bulk or cement may have an aqua color. If a white colored grout, plaster, caulk or cement is desired, the concentration of copper sulfate in the solution should be from about 1000 to about 7500 ppm. The proportions of aqueous germicidal composition in the fresh grout, plaster, caulk or cement may vary, but is sufficient to give a wet grout or fluid plaster or cement having a consistency of the desired level. The fluid grout, plaster, caulk or cement is then applied to the tiles, lathes, forms or otherwise, and allowed to solidify and cure. The resulting hard porous substance such as cured grout, plaster, caulk or cement is thus impregnated with a germicidal copper complex and unreacted copper sulfate which are capable of retarding the growth of fungus for extended periods of a year or more. Generally, the proportion of copper compound in the cured hard porous substance is from about 0.001 to about 0.75% and preferably from about 0.05 to about 0.6% by weight of the porous substance if substantially uncolored grout is desired. However, if color is not objectional, the proportion of copper compound in the cured hard porous material may range up to about 10% by weight.

Typical mortar mixes used for installing glazed ceramic tile on walls range from about one part portland cement, ½ part hydrated lime and 5 parts damp sand up to about one part portland cement, one part hydrated lime and 7 parts damp sand by volume. Formulation for ceiling and floor installation will vary with the conditions. For example, a typical ceiling mix contains one part portland cement, 2½ parts dry sand or 3 parts damp sand and ½ part hydrated lime by volume. A typical floor or deck mortar is comprised of one part portland cement, 5 parts sand or 6 parts damp sand and 1/10 part hydrated lime by volume.

The term "ppm" used throughout the description and claims is an abbreviation for "parts per million by weight".

As indicated above, the germicidal solution is effective in the treatment of fungus such as mold and mildew, particularly the orange mold and black mold. In addition, it is effective in the treatment of surfaces which are contaminated with algae and bacteria. Although the invention has been described with respect to the treatment of bathroom components such as bathtubs and ceramic tiled shower stalls and components thereof, one skilled in the art will recognize that the novel germicidal solution of this invention can also be used in the decontamination of other hard surfaces, such as refrigerator interiors and exteriors, toilets, stoves, and the like. In addition, the novel germicidal solutions of this invention, particularly those of lower concentrations of copper sulfate, may be used in the treatment of swimming pools to prevent the growth of algae and to minimize bacteria growth. Furthermore, where color is not a problem, the novel germicidal solutions of this invention may be added in small proportions to paint in order to prevent mold from growing on the painted surfaces.

Although the invention has been described primarily with respect to the use of copper sulfate as the water soluble copper compound, it should be understood that other water soluble copper compounds mentioned above may be used to replace all or part of the copper sulfate in order to obtain the same or similar results with respect to the treatment of fungus, algae and bacteria. If another copper compound is used, it is used in approximately the same proportions as recited above with respect to the copper sulfate.

The following examples are presented in order to define the invention more fully without being limited thereby. All parts and percentages are by weight, unless otherwise specified.

EXAMPLE 1

To one gallon of water were added 1.57 ounces of commercial grade bluestone (cupric sulfate pentahydrate), which corresponds to one ounce of anhydrous copper sulfate, or 0.75% cupric sulfate solution. About four ounces of Ivory Brand dishwashing liquid were added to the aqueous copper sulfate solution and mixed until a homogeneous solution was obtained. This dishwashing liquid was an unbuilt, high-sudsing, light-duty liquid detergent composition prepared in accordance with the procedure of U.S. Pat. Nos. 3,179,598, 3,179,599 and 3,024,273.

An enclosed title shower stall with a glass door and no ventilation other than a ⅛ inch opening at the bottom and about a 7½ inches opening at the top of the door was treated with the above prepared solution. A fiber brush was dipped into the above prepared copper sulfate solution and rubbed against the surface of the grout seams of the shower stall until wet. After about 5 minutes, the grout seams were wiped with a soaking wet rag to remove loose fungus and then wiped with a slightly damp cloth until dry. After more than a year following this treatment, no black fungus appeared on over 90% of the grout seams.

For purposes of comparison, when the same shower stall was cleaned with a solution which contained only a chlorinated detergent to remove all fungus on the grout seams, the black fungus reappeared and covered about 70% of the grout seams within about 7 days.

EXAMPLE 2

The procedure of Example 1 was repeated except that the Ivory Brand dishwashing liquid was replaced with a wetting agent, $NaOOCCH(SO_3NA)-CH_2CON(C_{18}H_{37})CH(COONa)CH_2COONa$ (Aerosol 22). After one year of treatment, formation of fungus in the shower stall did not occur on over 90% of the tile seams.

EXAMPLE 3

Dried uncured powdered grout was admixed with sufficient aqueous solution of copper sulfate of a concentration of 0.75% cupric sulfate until the wet grout was of a suitable consistency to apply to a tile seam about two feet long in the corner of the shower stall of Example 1. The grout was allowed to dry and the shower was subjected to normal use. After more than one year of use, the grout seam thus treated was completely free of mold.

EXAMPLE 4

To the germicidal solution of Example 1 was added about 80 drops of bluing. This solution was applied to the tile of Example 1 in the same manner and it was found that not only mold growth was prevented over 90% of the grout seams for over one year but also the grout seams remained white after the application of the germicidal solution of Example 1 and no aqua color was noted.

EXAMPLES 5–7

The procedure of Example 1 was repeated except that the Ivory Brand dishwashing liquid was replaced with the surfactants listed below in the proportionsl-isted below:

| Example | Surfactant | Per Cent of Surfactant | Per Cent of Copper Sulfate | Per Cent of Ammonium Lauryl Sulfate |
|---|---|---|---|---|
| 5 | Orvus K | 2.96 | 0.76 | 1.11 |
| 6 | Igepon T-33 | 2.05 | 0.76 | |
| 7 | Orvus K | 1.025 | 0.76 | 0.38 |
| | Igepon T-33 | 1.025 | | |

After more than two years of treatment of the tile grout, formation of fungus did not occur on over 90% of the tile seams. In addition, a synergistic effect was noted in that the proportion of Orvus K could be reduced by nearly one-half when admixed with Igepon T-33, as in Example 7.

EXAMPLE 8

One germicidal solution of Example 7 was applied to ten glazed ceramic tiles in accordance with the "Hard Surface Mildew Fungistatic Test Method" (Revised 12-1-70) prepared by the Environmental Protection Agency. The treated tiles were conducted to the *Aspergillus Niger* solution at 25° C for 14 days and no mold or fungus appeared on the tiles during this period. In contrast, ten additional tiles without treatment with the novel fungistat solution of Example 7 were contacted with the *Aspergillus Niger* solution and fungus growth appeared on at least 50% of each tile surface within the first 7 days of contact.

EXAMPLE 9

An aqueous solution was prepared containing 7.1% copper sulfate and 0.1% of a commercial solution of sodium-N-methyl-N-oleoyl taurate having the composition described above for Igepon T-33 surfactant. Ten milliliters of the resulting solution was admixed with 190 ml. of tap water and 155 ml. of the resulting solutions were admixed with 454 grams of grout to form a mortar mix. The mix was poured into 10 molds having an opening of 1¾ × 1¾ × ¼ inch and a spatula was used to remove excess mortar. The mortar was air dried for about one week in the molds until hard tiles were formed.

For purposes of comparison, another set of 10 tiles were made by mixing 454 grams of mortar with 150 ml. of tap water.

Both sets of tiles were subjected to the EPA test described in Example 8, along with 10 standard untreated glazed ceramic tiles.

After more that 40 days, none of the tiles prepared with the novel fungistat solution of this invention had any fungus on the surfaces. In contrast, of the tiles prepared from grout and tap water and only, 8 of the 10 tiles had fungus on the surface of each tile within 14 days. For further comparison, all 10 of the glazed tiles had fungus on more than 50% of the surface of each after 7 days. This comparative test shows that when the novel fungistat solution of this invention is used to prepare mortar for use in fixing tiles fungus growth on the grout will be substantially inhibited.

What is claimed and desired to be secured by Letters Patent is:

1. A process for inhibiting the growth of microorganisms on porous surfaces containing free alkaline hydroxide, said porous surface being a member selected from the group consisting of grout, caulk, plaster and cement, which comprises applying to said porous surface an aqueous germicidal solution containing from about 100 to about 100,000 parts per million of copper sulfate and from about 0.05 to about 6% by weight of a water soluble anionic nitrogen-containing surfactant, whereby a water insoluble tribasic cupric sulfate complex forms on said porous surface.

2. The process of claim 1 wherein said aqueous solution contains from about 100 to about 10,000 parts per million by weight of copper sulfate and from about 0.08 to about 5% by weight of said surfactant.

3. The process of claim 2 wherein said surfactant is a member selected from the group consisting of:

a. a liquid detergent consisting essentially of
  1. from about 20% to about 40% by weight of the composition of a sulfate detergent surfactant having the following formula $$R-(C_2H_4O)_x-SO_4-Me$$

wherein R is a straight chain alkyl group having from 10 to about 14 carbon atoms with at least 50% of said alkyl groups having 12 carbon atoms, *x* is a number from zero to about four, and Me is a member selected from the group consisting of monoethanolamine, diethanolamine, ammonium, sodium and potassium cations,
  2. from about 5% to about 20% by weight of the composition of a trialkyl amine oxide having one straight chain alkyl group having from about 10 to about 14 carbon atoms and two short chain alkyl groups having 12 carbon atoms in an amount such that the weight ratio of sulfate detergent surfactant to amine oxide is from about 1/1 to about 7/1, 3. from about 2% to about 10% by weight of the composition of an alkyl glyceryl ether sulfonate having a straight chain alkyl group having from about 10 to about 14 carbon atoms with at least 50% of said alkyl group having 12 carbon atoms, the cation of said sulfonate being a member selected from the group consisting of monoethanolamine, diethanolamine, triethanolamine, ammonium, sodium, and potassium cations and mixtures thereof, the amount of said sulfonate being at least 20% of the amount of said amine oxide,
  4. at least about 5% by weight of the composition of a solubilizing agent selected from the group consisting of methyl, ethyl, n-propyl, and isopropyl alcohols,
  5. and the balance water.

b. a fatty acid amide of sodium hydrocarbon sulfonate
c. ammonium lauryl sulfate and
d. mixtures thereof.

4. The process of claim 3 wherein said surfactant is a fatty acid amide of sodium methyl taurine.

5. The process of claim 3 wherein said surfactant is ammonium lauryl sulfate.

6. The process of claim 3 wherein said surfactant is a mixture of a fatty acid amide of sodium methyl taurine and ammonium lauryl sulfate.

* * * * *